United States Patent
Krause

(10) Patent No.: US 8,747,117 B2
(45) Date of Patent: Jun. 10, 2014

(54) RAPID VISUAL CUING APPARATUS FOR CARDIAC EKG RHYTHMS

(75) Inventor: Gary Krause, Racine, WI (US)

(73) Assignee: EKG Concepts, LLC, Racine, WI (US)

( * ) Notice: Subject to any disclaimer, the term of this patent is extended or adjusted under 35 U.S.C. 154(b) by 583 days.

(21) Appl. No.: 13/110,160

(22) Filed: May 18, 2011

(65) Prior Publication Data

US 2012/0065531 A1    Mar. 15, 2012

Related U.S. Application Data

(63) Continuation-in-part of application No. 12/880,544, filed on Sep. 13, 2010.

(51) Int. Cl.
*G09B 23/28* (2006.01)

(52) U.S. Cl.
USPC .......................................................... 434/262

(58) Field of Classification Search
USPC ......... 434/156, 157, 262, 365, 366, 367, 428, 434/429; 283/34, 35, 46, 61, 62, 115, 117, 283/900
See application file for complete search history.

(56) References Cited

U.S. PATENT DOCUMENTS

| | | |
|---|---|---|
| D215,649 S | 10/1969 | MacLachlan et al. |
| 3,792,542 A | 2/1974 | Cohan |
| 4,165,890 A | 8/1979 | Leff |
| D260,153 S | 8/1981 | Koltys |
| D334,597 S | 4/1993 | Busquets |
| 5,636,873 A | 6/1997 | Sonsteby |
| 5,713,739 A | 2/1998 | Yu |
| D396,882 S | 8/1998 | Neal, Jr. |
| 5,984,368 A | 11/1999 | Cain |
| 5,984,685 A | 11/1999 | Portnoy |
| 6,024,571 A | 2/2000 | Renegar |
| 6,354,985 B2 * | 3/2002 | Huber .......................... 493/458 |
| D456,910 S | 5/2002 | Clark et al. |
| 6,406,922 B2 | 6/2002 | Casterlin et al. |
| 6,746,052 B1 * | 6/2004 | Reynolds ........................ 283/61 |
| D561,187 S | 2/2008 | Kunioka et al. |
| D587,145 S | 2/2009 | Nakatsubo et al. |
| D588,029 S | 3/2009 | Nakatsubo et al. |
| D589,380 S | 3/2009 | Nakatsubo et al. |
| D596,965 S | 7/2009 | Nakatsubo et al. |
| D613,419 S | 4/2010 | Coyne, III et al. |
| D636,023 S | 4/2011 | Krause |
| D659,189 S | 5/2012 | Krause |

(Continued)

OTHER PUBLICATIONS

Basic Arrhythmia Flashcard Set, http://www.mc.vanderbilt.edu/root/vumc.php?site=vanderbiltnursing&doc=18729.

(Continued)

*Primary Examiner* — Kurt Fernstrom
(74) *Attorney, Agent, or Firm* — Reinhart Boerner Van Deuren s.c.

(57) ABSTRACT

The present invention is a visual cuing device which allows users to rapidly and easily identify ECG/EKG cardiac arrhythmias and twelve lead ECG/EKG arrhythmias. A visual cuing device contains a plurality of panels with a plurality of graphically displayed ECG/EKG abnormalities alternated with visually high-contrast, solid colored text sections. A visual cuing device may also contain additional tools, such as a heart rate reference line, time reference line or baseline window to aid in analysis and interpreting ECG/EKG strips. A visual cuing device may also be adapted to display using a touch screen or other user interface.

20 Claims, 9 Drawing Sheets

(56) References Cited

U.S. PATENT DOCUMENTS

| | | |
|---|---|---|
| 2002/0125712 A1* | 9/2002 | Felderman ............... 283/34 |
| 2005/0285384 A1* | 12/2005 | Judson ..................... 283/34 |
| 2008/0038704 A1 | 2/2008 | Aruffo et al. |
| 2008/0081322 A1 | 4/2008 | Fosbrook |
| 2008/0153071 A1 | 6/2008 | Stillman |
| 2012/0064496 A1 | 3/2012 | Krause |
| 2013/0052624 A1 | 2/2013 | Saps et al. |

OTHER PUBLICATIONS

U.S. Appl. No. 29/386,658, filed Mar. 3, 2011, Krause.

U.S. Appl. No. 29/392,143, filed May 18, 2011, Krause.

The ECG Ruler, American Heart Association, believed to be publicly available before Sep. 2009, 1 page.

Hawelka, "Cardiac Arrhythmia—Medical Pocket Cards," Jan. 10, 2007, in Mar. 19, 2013 Office Action in copending U.S. Appl. No. 12/880,544, 4 pages.

* cited by examiner

RAPID VISUAL CUING APPARATUS FOR CARDIAC EKG RHYTHMS

CROSS-REFERENCE TO RELATED APPLICATIONS

This application is a continuation-in-part application that claims priority to U.S. Nonprovisional application Ser. No. 12/880,544 filed Sep. 13, 2010.

FIELD OF INVENTION

The present invention relates to the field of medical devices, and more specifically to a visual device for rapidly identifying cardiac arrhythmias.

TERMS OF ART

Figure 1:
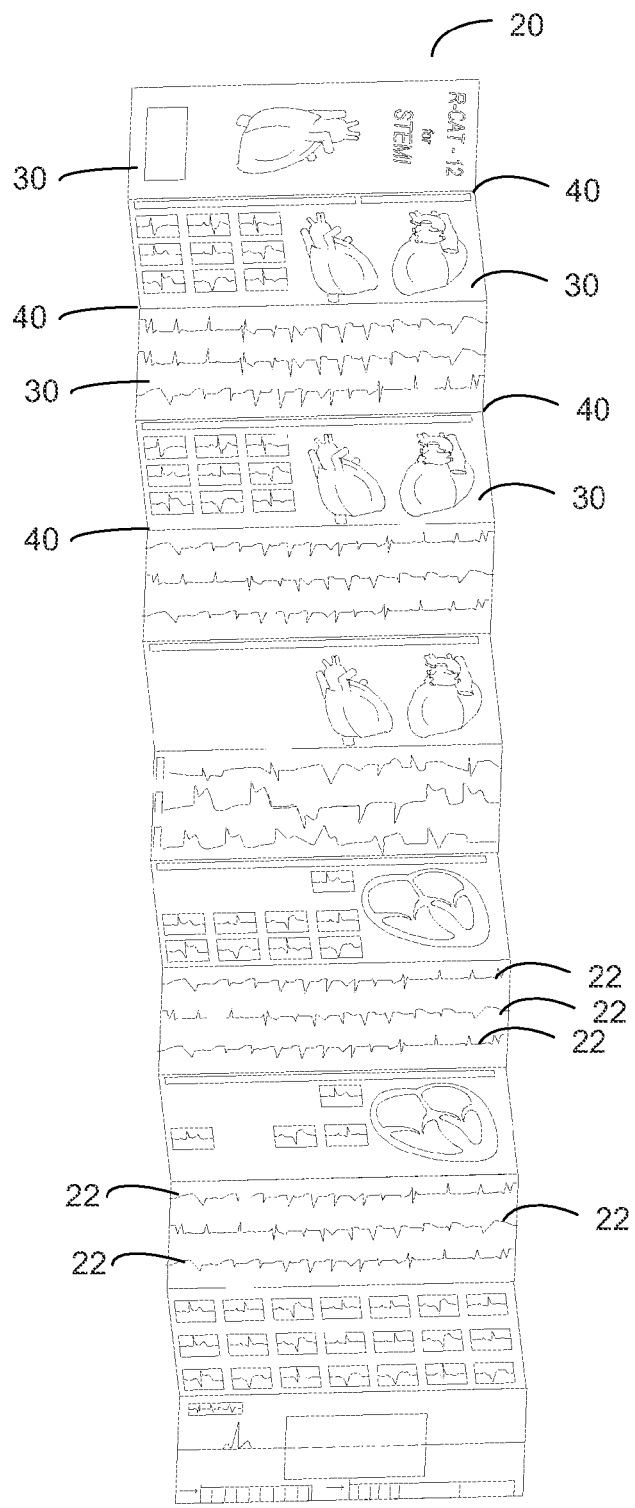
FIG. 1 is an exemplary embodiment of a rapid visual cuing apparatus.

As used herein, the term "artifact" is a term known in the art which refers to data in an ECG and EKG record or image which falsely reflects an arrhythmia. For example, artifacts may reflect phenomena resulting from normal patient activity, electrical interference, loose electrodes, etc.

As used herein, the term "baseline window" refers to a transparent, quasi-transparent or translucent portion of a visual cuing device which contains a straight line that may be held against an EKG strip or ECG strip to determine elevations and changes in rhythms compared to a baseline.

As used herein, the term "cardiac rhythm image" may be used to refer to both ECG/EKG arrhythmia images and twelve lead ECG/EKG arrhythmia images.

As used herein, the term "ECG/EKG strip analysis tool" refers to any tool which aids a user in reading, analysis and interpreting ECG/EKG strips. ECG/EKG strip analysis tools may include, but are not limited to, baseline windows, time reference lines and heart rate reference lines.

As used herein, the term "EKG strip" or "ECG strip" means any image produced by an electrocardiograph machine or instrument.

As used herein, the term "graphically displayed ECG/EKG abnormality" refers to an illustration or depiction of an ECG/EKG abnormality, such as an ECG/EKG arrhythmia or a twelve lead ECG/EKG arrhythmia, with ideal exemplary characteristics of the abnormality. Graphically displayed ECG/EKG abnormalities may include, but are not limited to, illustrations of normal sinus rhythm, sinus bradycardia, sinus tachycardia, sinus arrhythmia, sinus with ST depression, sinus with ST elevation, sinus rhythm with significant Q-wave, sinus with wide QRS and inverted T-wave, sinus arrest, atrial tachycardia, sinus with paroxysmal supraventricular tachycardia, Wolf Parkinson White Syndrome, atrial flutters, artifact, atrial fibrillation, multi atrial tachycardia, sinus with premature atrial contractions, sinus with premature junctional contractions, junctional escape rhythm, accelerated junctional rhythm, atrial pacing, ventricular pacing, ventricular pacing with failure to capture, atrial ventricular pacing, 1st degree heart block, 2nd degree type I, 2nd degree type II, 3rd degree heart block (complete heart block), 3rd degree AV block with junctional escape pacemaker, sinus with unifocal premature ventricular contractions, sinus with multi-focal premature ventricular contractions, sinus with episodes of non-sustained ventricular tachycardia, sinus with premature ventricular contractions converting to ventricular tachycardia (R on T), sustained ventricular tachycardia, Torsades de pointe, ventricular fibrillation, idioventricular rhythm, accelerated idioventricular rhythm, agonal rhythm (dying heart), ventricular standstill progressing to asystole inferior wall changes, septal wall changes, anterior wall changes, lateral wall changes, anterospetal wall changes, anterolateral wall changes, anterolateral wall injury, interior wall injury, septal wall injury, anterior wall injury, lateral wall injury, anteroseptal wall injury, ST elevation in inferior/lateral wall with reciprocal changes, left bundle branch block, and right bundle branch block.

As used herein, the term "heart rate reference line" refers to an illustration or other indication which a user may hold against an EKG strip or ECG strip to determine and measure a patient's heart rate.

As used herein, the term "high contrast" refers to characteristics of text and images which allow the text or images to be quickly and easily viewed. For example, high contrast colors may include, but are not limited to, black, white, red and yellow.

As used herein, the term "key characteristic" means those essential characteristics of a cardiac arrhythmia that are necessary for its identification.

As used herein, the term "order priority" means the order in which cardiac arrhythmias potentially pose risk to a patient based on generalized, non-treatment based assumptions.

As used herein, the term "panel" refers to viewable interface configured with contrasting color sections and high-impact images and alpha-numeric symbols demonstrated to maximize a viewer's ability to quickly comprehend information and reduce the viewer's analysis, response and/or reaction time.

As used herein, the term "sufficient time duration" refers to the time needed in order to establish a cardiac arrhythmia pattern at a characteristic heart rate. For most cardiac arrhythmias, a time duration of 4 to 8 seconds is sufficient to establish a pattern.

As used herein, the term "surface" refers to any stationary or mobile surface a user may removably or permanently secure a visual cuing device to. Surfaces may include, but are not limited to, tables, desks, emergency crash carts, nurses' stations, ECG/EKG devices, walls, doors, examination tables and patient beds.

As used herein, the term "textual indication" refers to any written description or supporting illustration for a graphically displayed ECG/EKG abnormality. Textual indications may include, but are not limited to an EKG abnormality name, a known EKG abnormality acronym, a known EKG abnormality abbreviation, key characteristics of an EKG abnormality, suggested treatment protocols, suggested medications, legend information, instructions on how to read and interpret ECG/EKG strips, heart diagrams, exemplary ECG/EKG waves, instructions for setting up a twelve lead ECG/EKG, and combinations thereof.

As used herein, the term "time reference line" refers to an illustration or other indication which a user may hold against an EKG strip or ECG strip to determine and measure cardiac pauses.

As used herein, the terms "twelve lead ECG" and "twelve lead EKG" refer to an ECG/EKG setup which traces twelve voltage differences, or leads, between electrodes placed on a patient. There are typically ten electrodes for a twelve lead ECG/EKG.

As used herein, the term "twelve lead ECG/EKG arrhythmia image" refers to an illustration or depiction of a heart beat or cardiac arrhythmia measured by a twelve lead ECG/EKG with ideal exemplary characteristics of the heartbeat or cardiac arrhythmia. Twelve lead ECG/EKG arrhythmia images may include, but are not limited to, normal sinus rhythm, inferior wall changes, septal wall changes, anterior wall changes, lateral wall changes, anterospetal wall changes, anterolateral wall changes, anterolateral wall injury, interior wall injury, septal wall injury, anterior wall injury, lateral wall injury, anteroseptal wall injury, ST elevation in inferior/lateral wall with reciprocal changes, left bundle branch block, and right bundle branch block.

As used herein, the term "visual cuing device" means a rigid display with illustrations depicting ideal cardiac rhythms and ECG/EKG abnormalities adapted to help a user quickly and easily compare the illustrations to actual cardiac rhythms and arrhythmias in a medical care setting. A visual cuing device may contain a single panel, such as a poster, or multiple panels.

BACKGROUND

Electrocardiography (ECG or EKG) is a representation of the activity of the heart captured and externally recorded by skin electrodes on an electrocardiographic device. Electrocardiography is displayed on computer screens and, equally commonly, on paper printouts that can be torn off of an electrocardiography machine (which typically includes a printer). The activity is represented in a single line graph which reflects the rhythm of the heart.

An irregular heart pattern, as reflected on an ECG or EKG, is an arrhythmia, and can be fatal.

There are approximately fifty or more different arrhythmias, each represented by a distinctive line graph pattern. These line graph patterns must be viewed and interpreted visually by a human being who is capable of recognizing the line patterns of the arrhythmias. Although it is possible to have a machine interpret ECG or EKG patterns, reading machines cannot view the patient and correlate the patient's physical status with the information on the ECG or EKG reading.

Electrocardiograph machines are highly sensitive machines which detect minute electrical impulses, changes and patterns. Thus, a number of readings that would indicate arrhythmias are disregarded or interpreted in light of the patient's observable physical status.

For example, it is a common scenario that a monitor disconnect from a monitoring device and register an ECG or EKG rhythm that indicates that the patient's heart has stopped (e.g., a ventricular rhythm or asystolic rhythm.) Other common problems occur when a patient is active, e.g., brushing his or her teeth, seizing, experiencing chills, shaking or simply moving normally.

Electrocardiograph systems typically have monitors or alarm systems that emit an audible sound to alert nursing and other healthcare professionals to check the status of a patient.

"Artifact" is a term known in the art which refers to data in an ECG or EKG record or image which falsely reflects an arrhythmia. Artifacts may be caused by normal patient activity, electrical interference and loose electrodes.

Medical staff, technicians, doctors, nurses and nurse practitioners must be trained to interpret ECGs and EKGs, both in the context of their graphical representations and the observable status of the patient. Interpretation of ECG's and EKG's graphical representations requires extensive training and visual memorization skills in order to memorize the line patterns. Many excellent nurses and physicians have difficulty quickly recognizing complex patterns of a single line, which is a skill required for recognizing an ECG or EKG pattern.

In emergency and high pressure situations, valuable time can be lost and deadly errors can be made as a result of misidentifying ECG's and EKG patterns.

Currently many companies produce visual cuing devices and flip charts. For example, Channing Bete Company and American Heart Association manufacture and distribute various templates, charts and books to be used by healthcare professionals as study and reference tools. However, these aids are not useful in actual patient monitoring settings. It is impractical for nurses to flip through books or look up fifty or more common arrhythmias while competently caring for patients.

Additionally, it is difficult for nurses and other healthcare professionals to efficiently monitor heart rhythms and reliably record them in a patient's chart. This means that valuable diagnostic data is lost. For example, it is cumbersome and time consuming for nurses to quickly (1) print out an ECG and EKG image which may reflect an arrhythmia; (2) label the document with the name of the arrhythmia that occurred; and (3) place the printout in the patient's electronic file.

In various medical monitoring environments (hospitals, clinics, long-term care centers, assisted living facilities, ambulances, flight for life, etc.), medical personnel of varying experience levels may be employed. Additionally, certain arrhythmias may present infrequently and are prone to misdiagnosis for this reason.

In hospital settings, dedicated technicians may be assigned to monitor electrocardiographic equipment; currently there is no way to monitor the accuracy and/or error rate of such personnel because their visual identification cannot be easily or economically recorded for spot-checking by supervisory personnel.

It is desirable to have a reliable system which allows a physician, nurse or technician to instantly recognize one of approximately 41 or more arrhythmias by name and communicate and/or document the rhythm and respond accordingly.

It is further desirable to efficiently capture ECG and EKG data over time intervals sufficient for diagnosis.

It is further desirable to continuously monitor the accuracy of professional staff in assessing and interpreting arrhythmias.

It is further desirable to have a reliable reference source which is easily carried by health care professionals to aid in the accuracy of assessing and interpreting arrhythmias and other cardiac rhythms.

SUMMARY OF THE INVENTION

The present invention is a visual cuing device allowing users to quickly and easily identify, compare and analyze ECG/EKG arrhythmias and twelve lead ECG/EKG arrhythmias. A visual cuing device according to the present invention may contain a plurality of exemplary graphically displayed ECG/EKG abnormalities on a plurality of comparative panels joined by reinforced pivotable seams. A visual cuing device may also contain additional tools, such as a time reference line, heart rate reference line and baseline window, to aid users in reading, analyzing and interpreting ECK/EKG strips.

DETAILED DESCRIPTION OF INVENTION

For the purpose of promoting an understanding of the present invention, references are made in the text to exemplary embodiments of an emergency cardiac arrhythmia identifying device and system, only some of which are described herein. It should be understood that no limitations on the scope of the invention are intended by describing these exemplary embodiments. One of ordinary skill in the art will readily appreciate that alternate but functionally equivalent electronic or non-electronic components and media may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

FIG. 1 is an exemplary embodiment of visual cuing device 20. Visual cuing device 20 is made of a plurality of comparative panels 30 joined at pivoting seams 40. Panels 30 contain a plurality of graphically displayed ECG/EKG abnormalities 22, which in the exemplary embodiment shown may be ECG/EKG arrhythmia images or twelve lead ECG/EKG images. In the exemplary embodiment shown, graphically displayed ECG/EKG abnormalities 22 may be on some panels 30 or all panels 30, and graphically displayed ECG/EKG abnormalities 22 may be on the front surface, back surface or both surfaces of panels 30.

In the exemplary embodiment shown in FIG. 1, visual cuing device 20 contains twelve panels 30, and is adapted to display a total of 41 ECG/EKG arrhythmia images 22. The 41 ECG/EKG arrhythmia images 22 contained on panels 30 correspond to the statistically most common arrhythmias. In further exemplary embodiments, visual cuing device 20 may contain more or fewer panels 30, with more or fewer ECG/EKG arrhythmia images 22. For example, visual cuing device 20 may contain additional panels 30 with additional ECG/EKG arrhythmia images 22 corresponding to statistically rare arrhythmias.

In other exemplary embodiments, panels 30 may contain twelve lead ECG/EKG arrhythmia images. For example, in some exemplary embodiments, visual cuing device 20 may contain thirteen panels 30 adapted to display eleven twelve lead ECG/EKG arrhythmia images 22.

In further exemplary embodiments, visual cuing device 20 may also contain legend information, including, but not limited to, instructions and illustrations on how to read and interpret graphically displayed ECG/EKG abnormalities 22 and characteristics of normal sinus rhythm. In still further exemplary embodiments, visual cuing device 20 may also contain additional ECG/EKG strip analysis tools, such as a time reference line, heart rate reference line, and baseline window.

In the exemplary embodiment illustrated in FIG. 1, visual cuing device 20 contains a plurality of panels 30 which fold in an accordion style into a thin pamphlet approximately 3 inches by 6 inches to 5 inches by 8 inches. This size is a critical minimum size in order to store visual cuing device 20 is a standard lab jacket or surgical scrub clothing compartment.

Figure 2A:
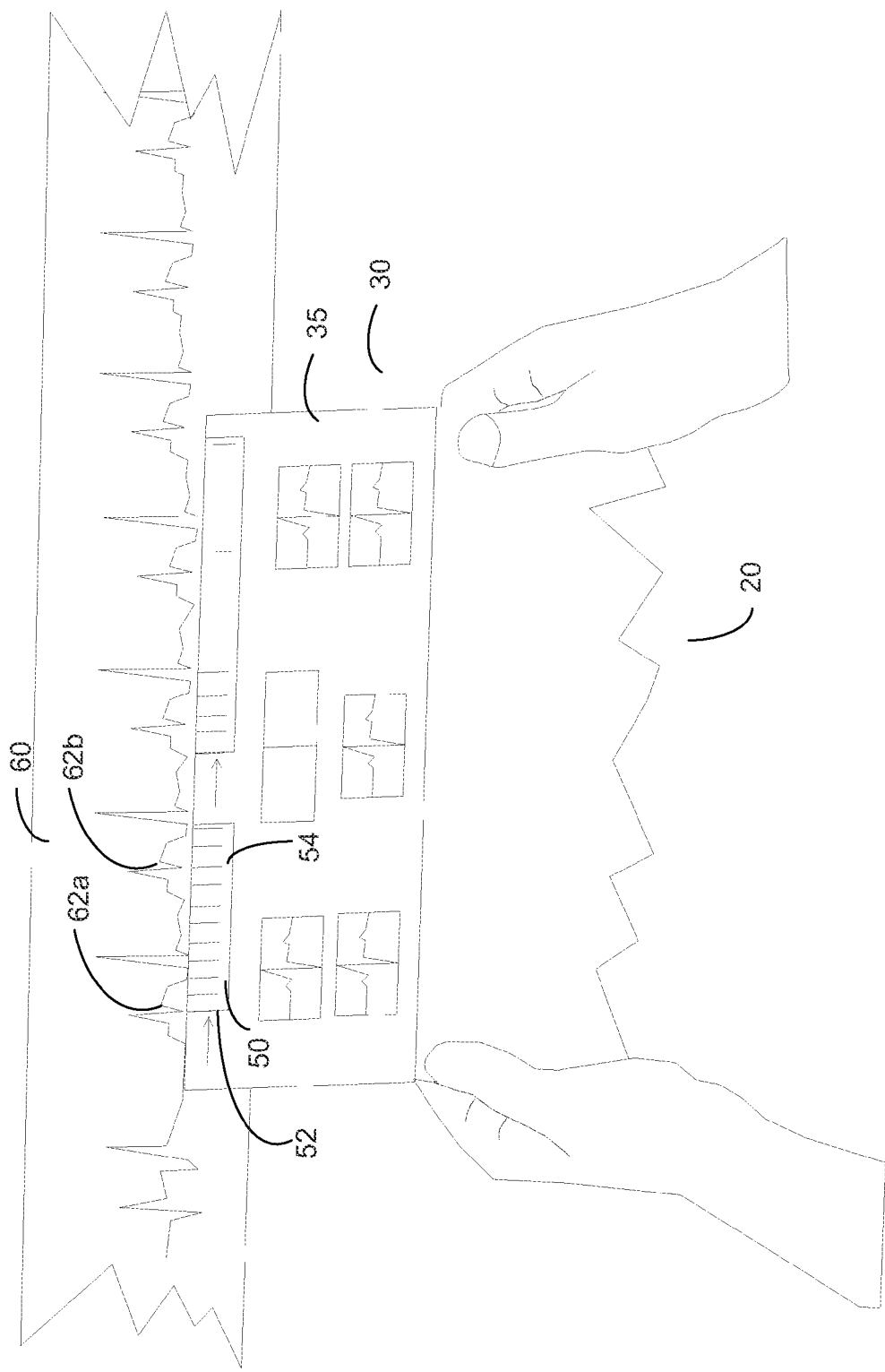
FIG. 2a is an exemplary embodiment of a heart rate reference tool of a rapid visual cuing apparatus in use.

FIG. 2a is an exemplary embodiment of heart rate reference line 50 ECG/EKG strip analysis tool in use. Panel 30 of visual cuing device 20 contains heart rate reference line 50 on an exterior edge of panel 30. Heart rate reference line 50 is a series of evenly spaced reference lines corresponding to time intervals of 0.2 seconds on a standard ECG/EKG strip. By placing heart rate reference line 50 on an ECG/EKG strip 60, as shown in FIG. 2a, a user can determine a heart rate. The initial marker of heart rate reference line 50 is aligned with a first cardiac event (i.e., initial P-wave, ST segment or QRS interval). To read the heart rate, a user reads the location of the next instance of the cardiac event along heart rate reference line 50. The corresponding rate on heart rate reference line 50 is the heart rate.

In the exemplary embodiment shown, for example, initial marker 52 of heart rate reference line 50 is aligned with cardiac event 62a. The next instance of cardiac event 62a occurs at 62b, which in the exemplary embodiment shown is aligned with marker 54. Each marker corresponds to a numerical heart rate, which is textually indicated in the proximity of the appropriate marker. The numerical heart rate corresponding with marker 54 is the heart rate for the exemplary embodiment illustrated in FIG. 2a.

Figure 2B:
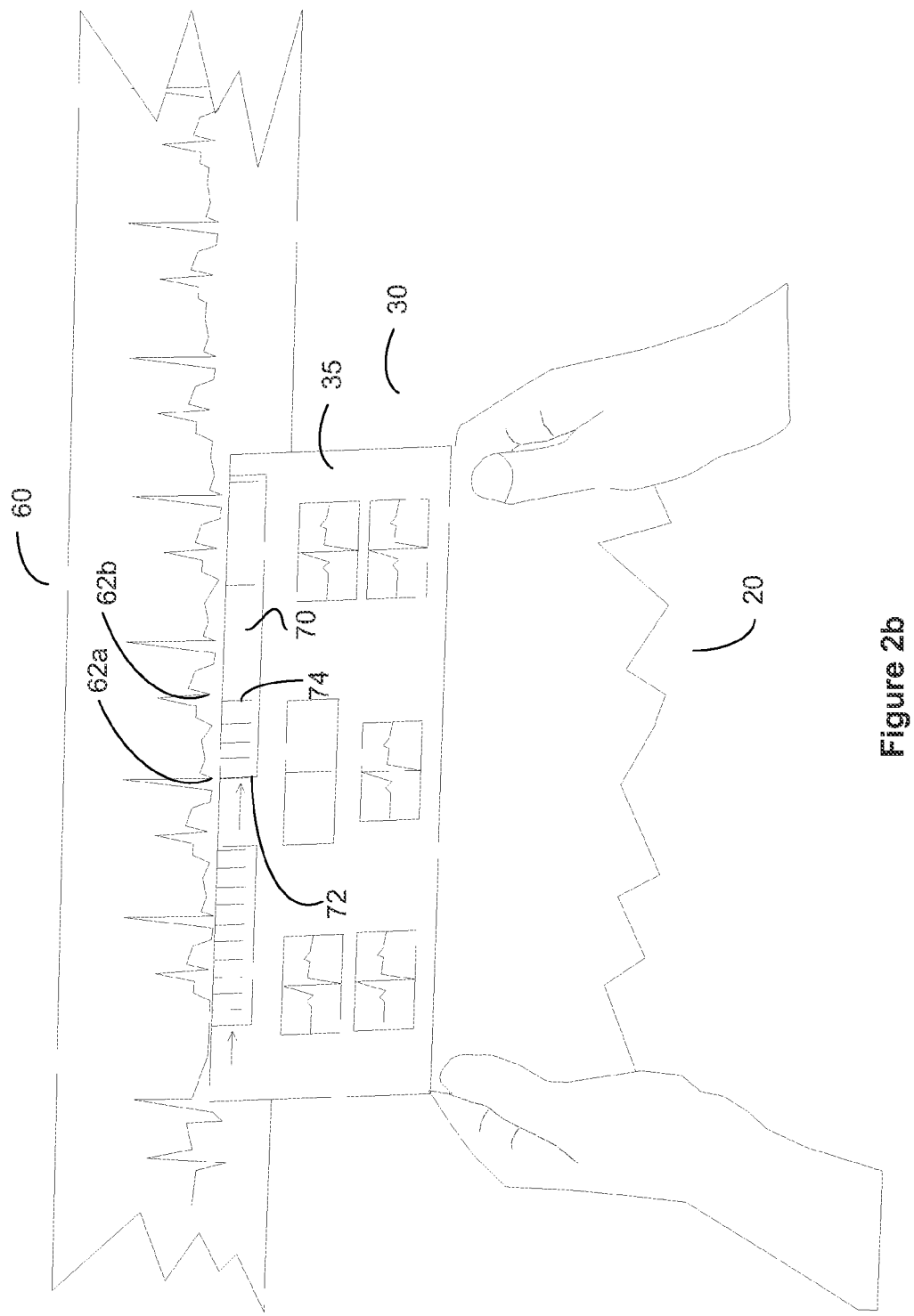
FIG. 2b is an exemplary embodiment of a time reference tool of a rapid visual cuing apparatus in use.

FIG. 2b is an exemplary embodiment of time reference line 70 ECG/EKG strip analysis tool in use. Panel 30 of visual cuing device 20 contains time reference line 70 on an exterior edge of panel 30. Time reference line 70 is a series of reference lines placed at expanding intervals which correspond to increasing time intervals from initial marker 72 as measured on a standard ECG/EKG strip. By placing time reference line 70 on ECG/EKG strip 60 as illustrated in FIG. 2b, a user can determine the time elapsed between two cardiac events.

In the exemplary embodiment shown, for example, a user may want to determine the time elapsed between cardiac event 62a and cardiac event 62b as illustrated on ECG/EKG strip 60. A user then aligns cardiac event 62a with initial marker 72 of time reference line 70 and determines the location of cardiac event 62b along time reference line 70. In the exemplary embodiment shown, cardiac event 62b aligns with marker 74. Each marker corresponds to a numerical time, which is textually indicated in the proximity of the appropriate marker. The numerical time associated with marker 74 is the time elapsed between cardiac events 62a and 62b for the exemplary embodiment illustrated in FIG. 2b.

Also illustrated in FIGS. 2a and 2b is legend portion 35 on panel 30. In the exemplary embodiments shown, legend portion 35 contains exemplary illustrations of a P-wave, PR interval, QRS interval, ST segment, and QT interval. In further exemplary embodiments, legend portion 35 may contain baseline indication, normative values and scaling information. In still further exemplary embodiments, legend portion 35 may comprise additional panels 30 and include textual and graphic instructions on how to use visual cuing device 20 and read and interpret ECG/EKG strips using visual cuing device 20.

Figure 2C:
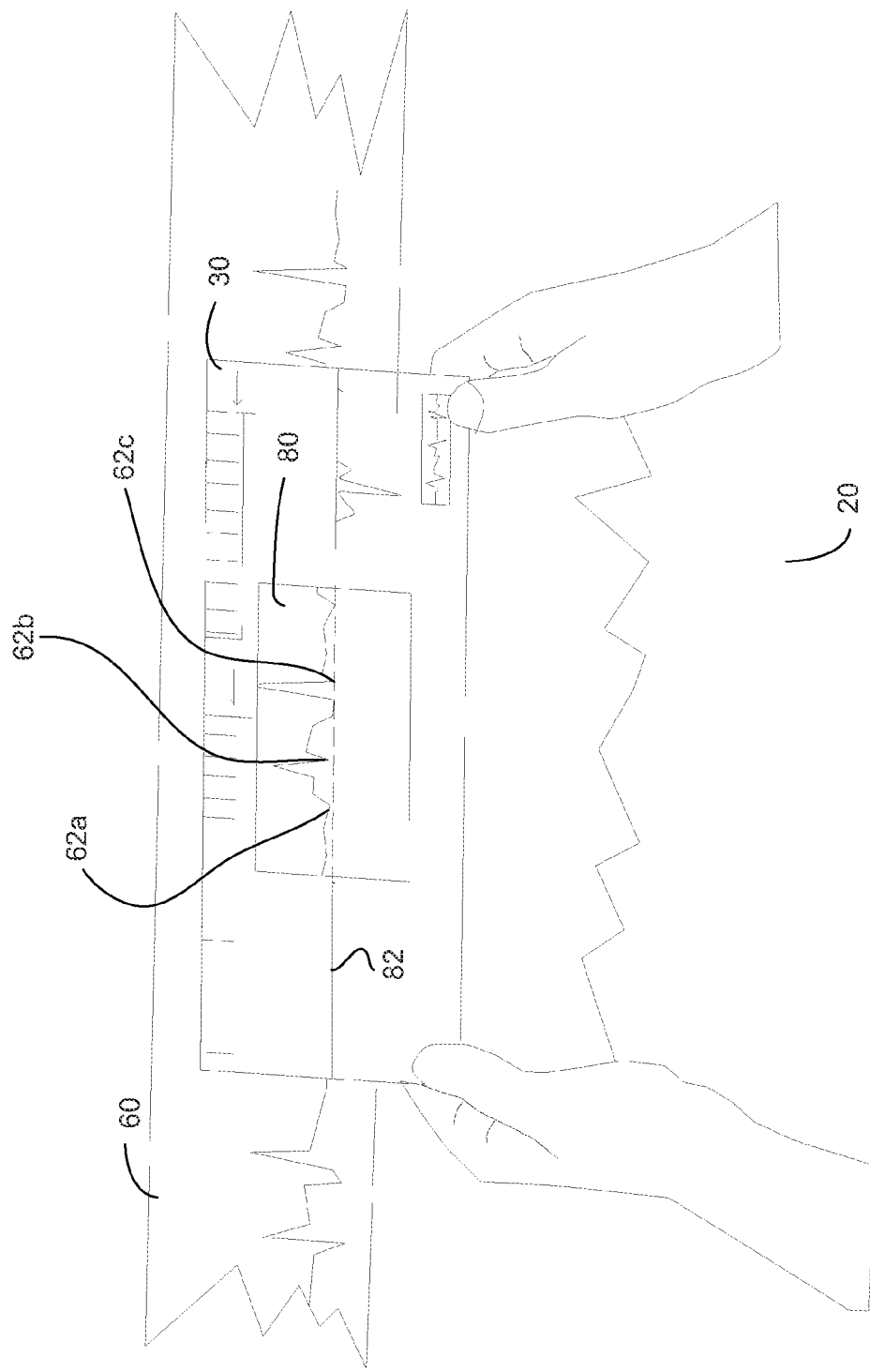
FIG. 2c is an exemplary embodiment of a baseline window tool of a rapid visual cuing apparatus in use.

FIG. 2c is an exemplary embodiment of baseline window 80 ECG/EKG analysis tool in use. Baseline window 80 on panel 30 is a transparent or quasi-transparent portion of panel 30 with baseline marking 82. In the exemplary embodiment shown, baseline marking 82 is illustrated as a solid line spanning the length of panel 30, becoming dashed only when printed on top of baseline window 30. In further exemplary embodiments, baseline marking 82 may be entirely solid or entirely dashed, and may span only a portion of baseline window 80 and panel 30. Baseline window 80 may aligned with a baseline of an ECG/EKG strip and used to determine elevations or depressions of cardiac events. In further exemplary embodiments, baseline marking 82 may be aligned with any cardiac event and used to determine elevations or depressions of future occurrences of the cardiac event.

In the exemplary embodiment illustrated in FIG. 2c, for example, baseline marking 82 of baseline window 80 is aligned with cardiac event 62a on ECG/EKG strip 60. Using baseline window 80, a user can then determine whether future occurrences of cardiac event 62a reach baseline marking 82. As illustrated in FIG. 2c, cardiac events 62b and 62c are future occurrences of cardiac event 62a. Cardiac event 62b does not reach baseline marking 82, while cardiac event 62c does. The consistency, elevation or depression of cardiac events on ECG/EKG strip 60 may be an important characteristic in analyzing ECG/EKG abnormalities.

In further exemplary embodiments, panel 30 with baseline window 80 may contain additional textual or illustrative information to help a user in using baseline window 80. For example, baseline marking 80 may include an exemplary illustration of a normal sinus rhythm for comparison purposes. In still further exemplary embodiments, panel 30 may contain exemplary illustrations of common ECG/EKG abnormalities characterized by changes in ECG/EKG pattern relative to a baseline. In yet further exemplary embodiments, panel 30 may contain textual instructions on how to use baseline window 80 or other analytical or comparative information.

Figure 3A:
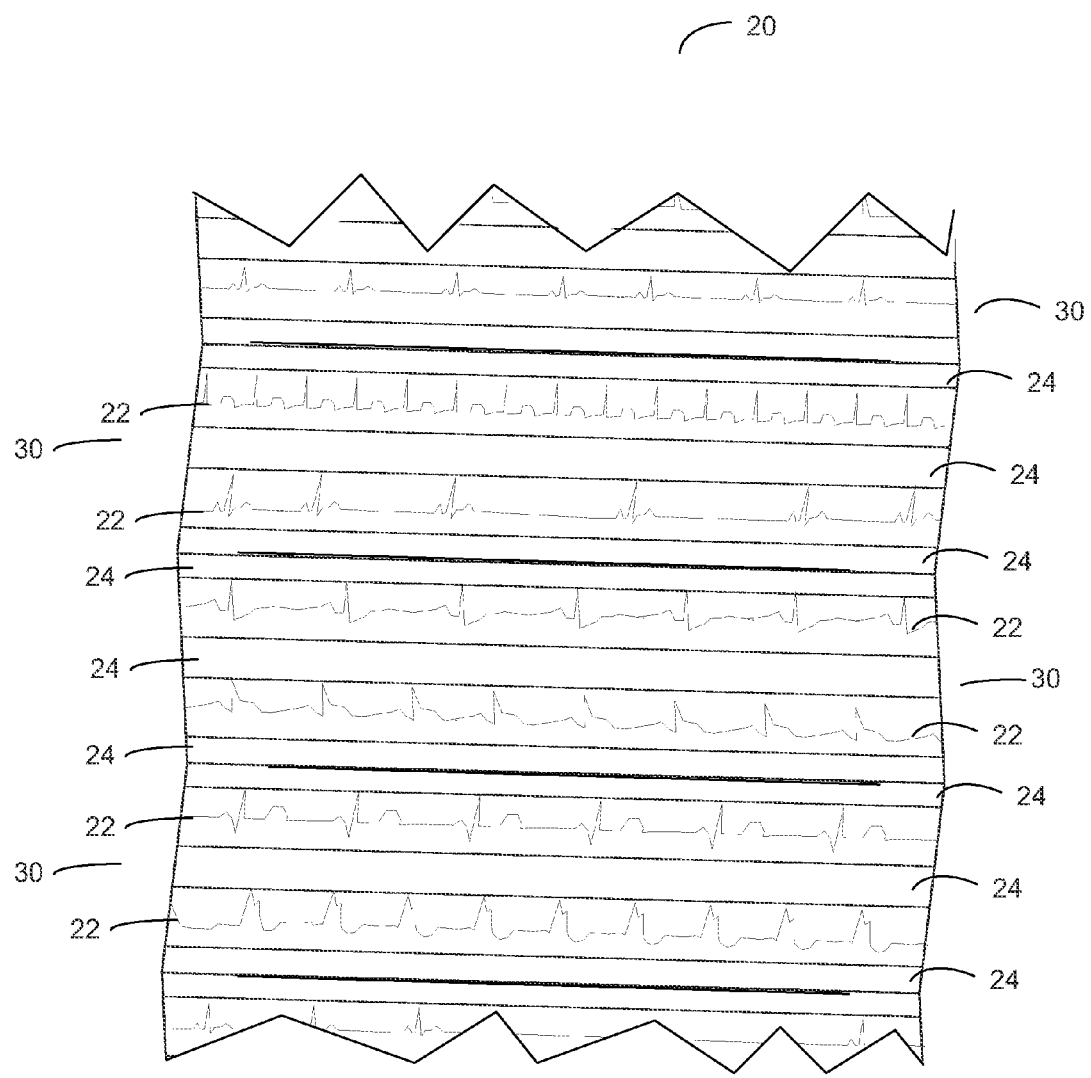
FIG. 3a is an exemplary embodiment of a portion of a rapid visual cuing apparatus.

FIG. 3a is an exemplary embodiment of comparative panels 30 for visual cuing device 20 with graphically displayed ECG/EKG abnormalities 22 alternated with high-contrast, solid-colored text sections 24. As illustrated in FIG. 3a, each comparative panel 30 contains two graphically displayed ECG/EKG abnormalities 22 and three high-contrast, solid-colored text sections 24. In further exemplary embodiments, panels 30 may contain fewer high-contrast, solid-colored text sections 24, so long as each graphically displayed ECG/EKG abnormality 22 is alternated with at least one high-contrast, solid colored text section 24.

In the exemplary embodiment shown in FIG. 3a, each graphically displayed ECG/EKG abnormality 22 is displayed over a duration of at least six seconds. Six seconds is a necessary time interval in order to display a sufficient number of cardiac complexes to identify an ECG/EKG pattern. Because each panel 30 has a length of no less than 5.5 inches and a width of no less than 1 inch, each graphically displayed ECG/EKG abnormality must be scaled to between 50% and 100% of a standard ECG/EKG strip. Scaling ECG/EKG abnormalities 22 to less than 50% makes them difficult to rapidly visually identify by a user with vision within the normal range and compare to ECG/EKG strips, but some scaling is necessary in order to fit a minimum number of graphically displayed ECG/EKG abnormalities 22 on panels 30 and have visual cuing device 20 fit in a standard lab jacket or surgical scrub compartment.

However, as illustrated in FIGS. 2a and 2b, heart rate reference line 50 and time reference line 70 must be to scale with standard ECG/EKG strips because they are used to directly analyze ECG/EKG strips.

In the exemplary embodiment shown in FIG. 3a, graphically displayed ECG/EKG abnormalities 22 are in high contrast colors, such as black, white, red and yellow. Specifically, as illustrated in the exemplary embodiments in FIGS. 1-15, ECG/EKG abnormalities are shown in black on a white and/or red background. In some exemplary embodiments, graphically displayed ECG/EKG abnormalities may have key characteristics highlighted in a contrasting color, such as red or yellow, for rapid identification. Key characteristics may be highlighted or indicated in red. Using highly contrasting colors aids users in rapidly visually identifying ECG/EKG abnormalities and allows for rapid comparison to actual ECG/EKG strips.

As illustrated in FIG. 3a, graphically displayed ECG/EKG abnormalities 22 are alternated with high-contrast, solid colored text sections 24. Text sections 24 may contain any textual information, including, but not limited to, an EKG abnormality name, a known EKG abnormality acronym, a known EKG abnormality abbreviation, key characteristics of an EKG abnormality, instructions on how to read and interpret ECG/EKG strips, heart diagrams, exemplary ECG/EKG complexes, instructions for setting up a twelve lead ECG/EKG, and any other information which may be displayed textual to aid a user in comparing ECG/EKG strips to visual cuing device 20. In still further exemplary embodiments, text sections 24 may also contain an exemplary illustration.

In the exemplary embodiments shown, text sections 24 are black and red font on a yellow background in order to contrast with the white and/or red background of graphically displayed ECG/EKG abnormalities 22. In further exemplary embodiments, other colors providing high contrast may be used.

As illustrated in FIG. 3a, visual cuing device 20 has a smooth surface using non-protruding seams to join panels 30. In the exemplary embodiment shown, the smooth surface is achieved by laminating visual cuing device 20 with a laminate having a thickness of 2 mm or less. In the specific exemplary embodiment described, the laminate has a thickness of 1.7 mm, which allows panels 30 to fold flat and remain in an open, upright and standing position if required. The laminate coating may also be adapted to be written on with a dry erase marker.

Figure 3B:
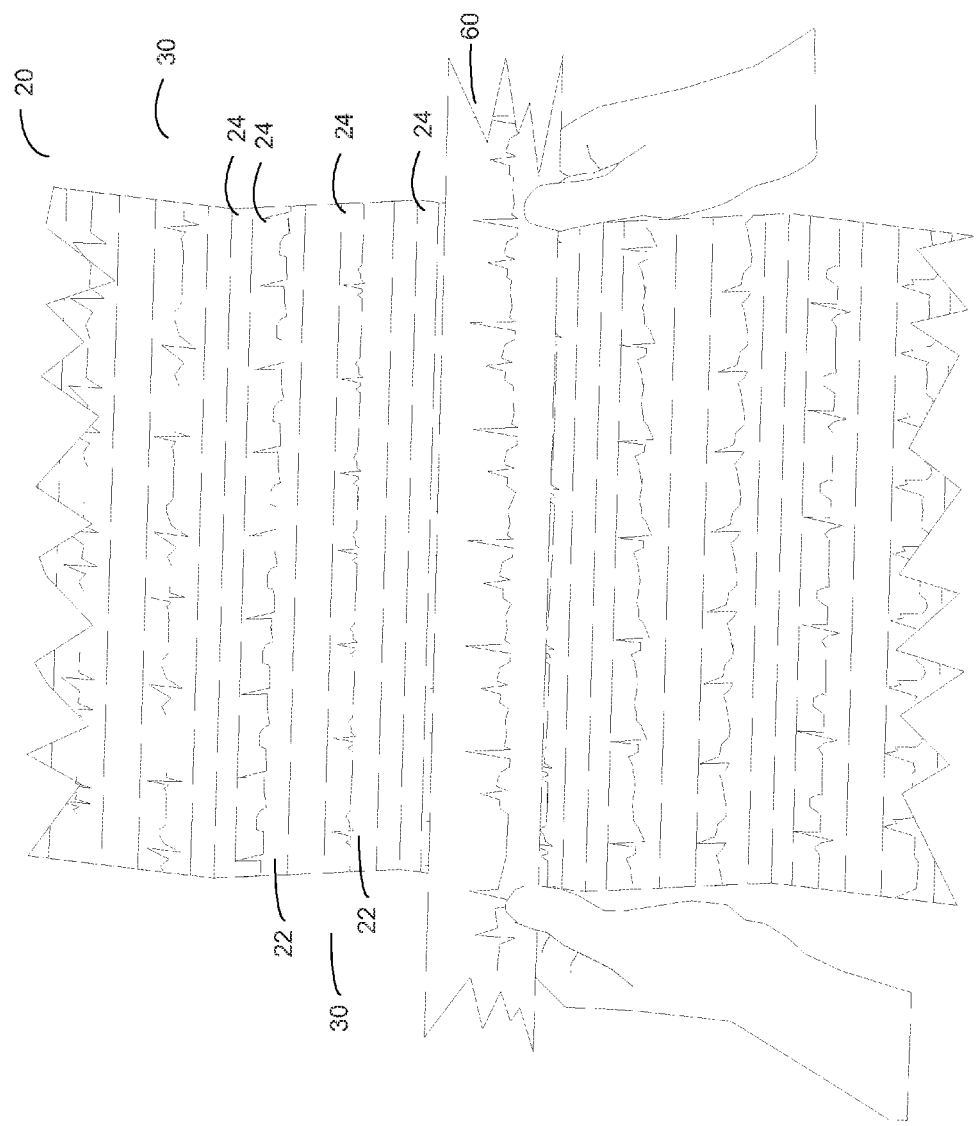
FIG. 3b is an exemplary embodiment of comparative panels for a rapid visual cuing apparatus.

FIG. 3b is an exemplary embodiment of comparative panels 30 in use to compare graphically displayed ECG/EKG abnormalities 22 to ECG/EKG strip 60. The smooth surface achieved by the laminate allows a user to physically slide ECG/EKG strip 60 along the surface of panels 30 to quickly and rapidly compare graphically displayed ECG/EKG abnormalities 22 to ECG/EKG strip 60.

Figure 4A:
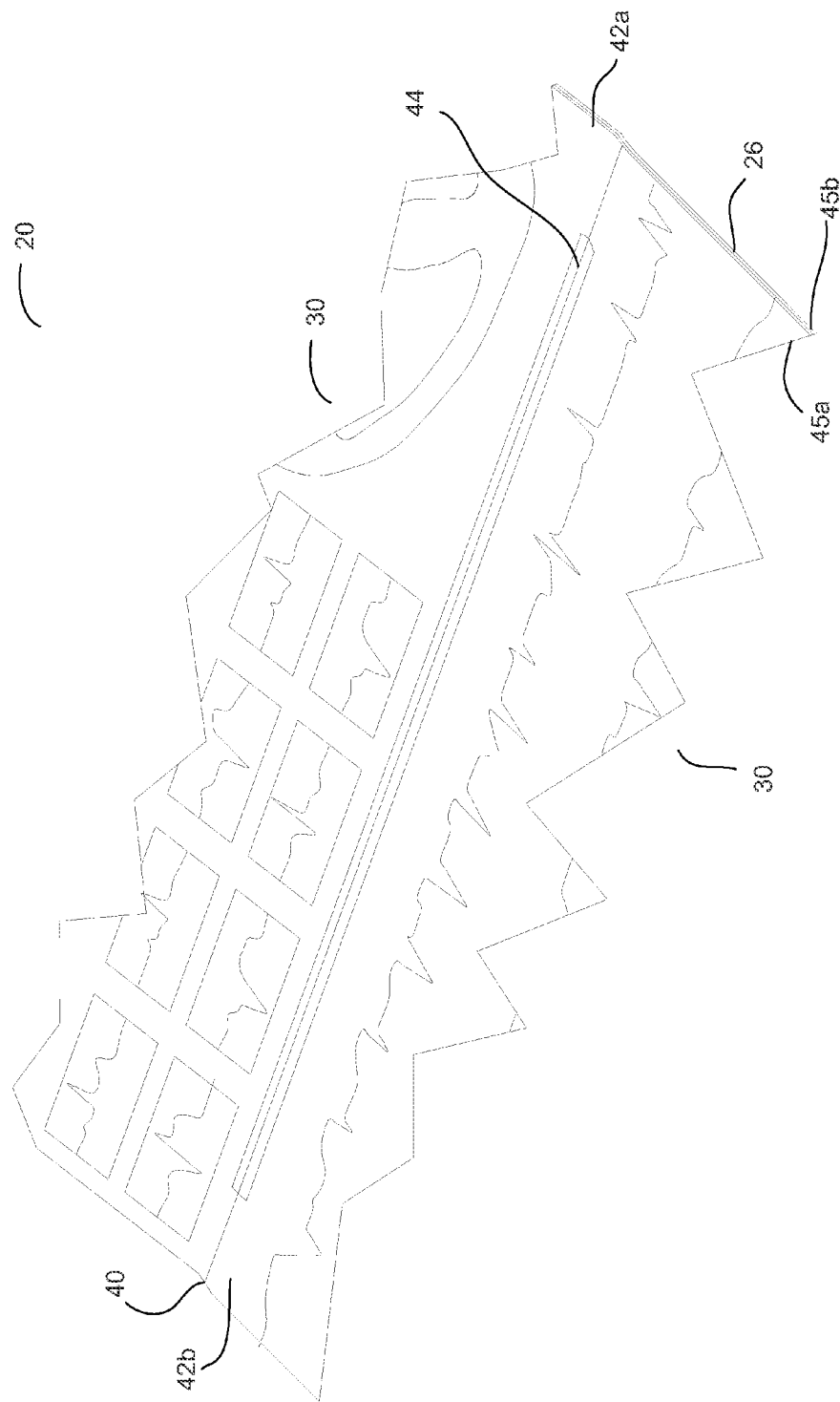
FIG. 4 is an exemplary embodiment of a reinforced seam for a rapid visual cuing apparatus.

FIG. 4a is an exemplary embodiment of pivoting seam 40 joining comparative panels 30. As illustrated in FIG. 4a, seam 40 contains continuous panel portions 42a, 42b which form physical junctions between panels 30, keeping panels 30 joined without lamination. Aperture 44 separates continuous panel portions 42a, 42b and removes a substantial volume of paper from each seam 40, which is necessary to allow visual cuing device 20 to fold flat. In the exemplary embodiment shown, aperture 44 is die cut, but in further exemplary embodiments, aperture 40 may be created by any cutting method known in the art to remove an interior portion of a paper substrate.

Seam 40 is then reinforced by lamination, resulting in a visual cuing device 20 having 3 primary layers. Paper substrate layer 26 contains the printed material of visual cuing device 20, and laminate layers 45a, 45b reinforce visual cuing device 20 and provide a smooth surface. Aperture 44, however, contains only two layers—laminate layers 45a, 45b. In the exemplary embodiment shown, laminate layers 45*a*, 45*b* are 1.7 mm thick. In further exemplary embodiments, laminate layers 45*a*, 45*b* may be no greater than 2 mm thick. A thickness of less than 2 mm is necessary in order to create a foldable seam which allows panels 30 to lay flat.

The structure of seam 40 also allows visual cuing device to be folded specifically in an accordion style and opened quickly with one hand.

In some exemplary embodiments, visual cuing device 20 is laminated by lamination methods known in the art using laminate material known in the art. In further exemplary embodiments, visual cuing device 20 may be laminated with a hard coat laminate substrate or heat sealed to create a smooth surface.

In yet further exemplary embodiments, visual cuing device 20 may contain additional layers or treatments, such as waterproofing or water resistance layers, anti-bacterial layers or other layers or treatments known in the art. In still further exemplary embodiments, visual cuing device 20 may contain a reinforced layer on a portion of visual cuing device 20 which allows visual cuing device to be secured to a surface, such as a desk, crash cart, or other surface which may allow quick access to visual cuing device when needed. Visual cuing device 20 may be secured to a surface through any means known in the art, including, but not limited to, binder rings, a pole, chain, clamp, cord, tethering device, lynch pin, adhesives, hook-and-loop fastener, and combinations of these securing means.

Figure 4B:
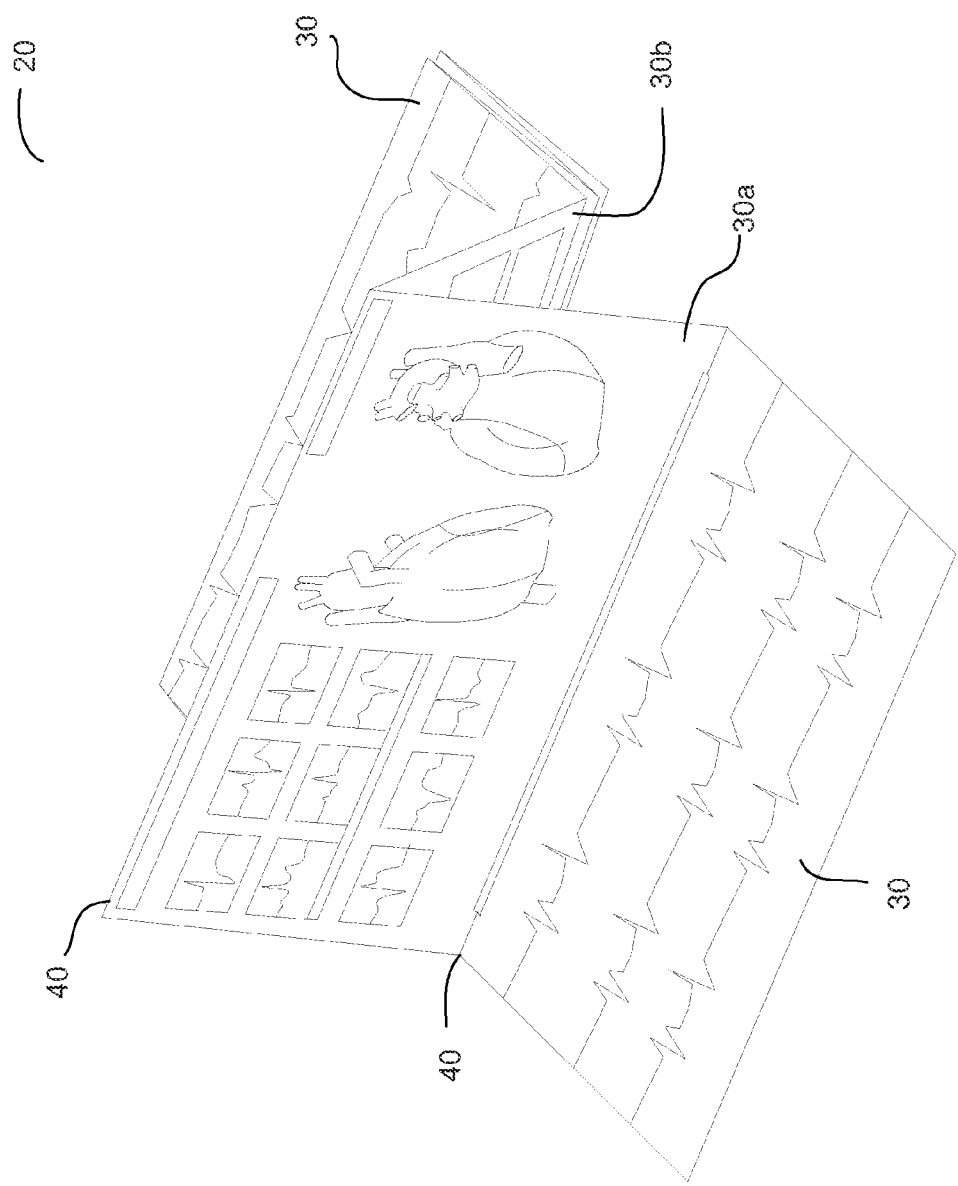

FIG. 4*b* is an exemplary embodiment of visual cuing device 20 partially opened with a selected panel 30 propped upright for comparison. In the exemplary embodiment shown, panels 30*a* and 30*b* are showed propped in a tent-like manner so that the surface of panel 30*a* is visible to a user without the user having to hold visual cuing device 20 in his or her hands. This may be beneficial if a healthcare provider would like to make notes in a patient's file comparing a patient's ECG/EKG strip to a graphically displayed ECG/EKG abnormality.

The structure of seams 40 and the rigidity of panels 30 created layers 45*a*, 26 and 45*b* allows panels 30*a*, 30*b* to remain standing upright while the remainder of visual cuing device 20 lays flat.

Figure 5:
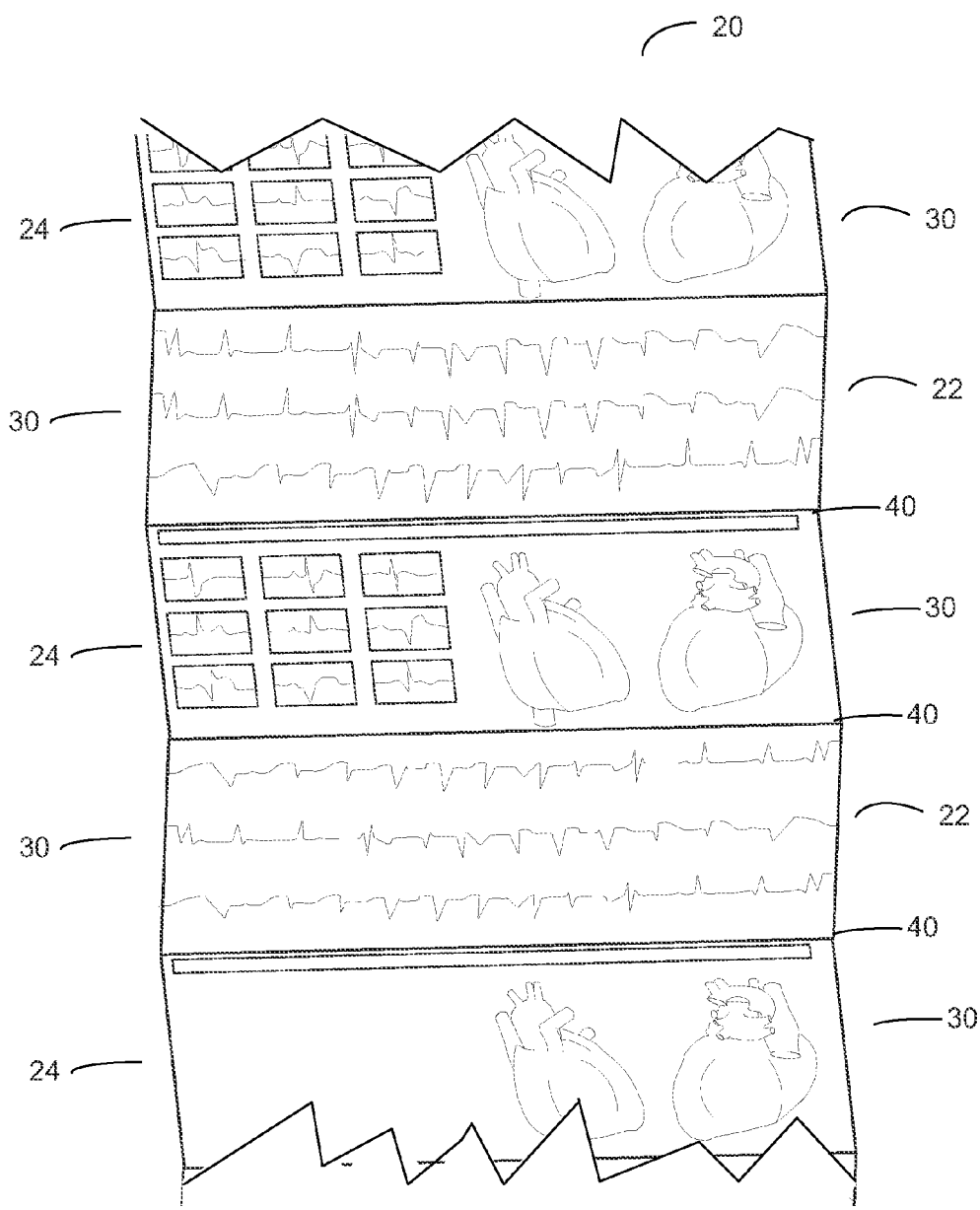
FIG. 5 is an alternative exemplary embodiment of a rapid visual cuing apparatus.

FIG. 5 is an alternative exemplary embodiment of visual cuing device 20 with comparative panels 30, including graphically displayed ECG/EKG abnormalities 22 and high-contrast, solid colored text sections 24. In the exemplary embodiments illustrated in FIGS. 3*a* and 3*b*, graphically displayed ECG/EKG abnormalities 22 are alternated with text sections 24, with at least one graphically displayed ECG/EKG abnormality 22 and at least one text section 24 on each panel 30. In the exemplary embodiment illustrated in FIG. 5, graphically displayed ECG/EKG abnormalities 22 are still alternated with high-contrast, solid colored text sections 24, but each graphically displayed ECG/EKG abnormality 22 and text section 24 is adapted to be the size of a panel 30.

In the exemplary embodiments described in FIGS. 1-5, visual cuing device 20 is implemented as a rigid display containing a plurality of comparative panels 30 with a plurality of graphically displayed ECG/EKG abnormalities. In some embodiment, ECG/EKG abnormalities may be categorically displayed based on common symptoms, commonly confused ECG/EKG abnormalities, or atrial to ventricular. In further exemplary embodiments, graphically displayed ECG/EKG abnormalities may be arranged in an order of priority based on generalized, non-treatment based assumptions of risk to a patient.

In further exemplary embodiments, visual cuing device 20 may be adapted to be displayed using a touch screen or other user interface. For example, graphically displayed ECG/EKG abnormalities may be arranged into categories or subcategories to allow a user to select a group of ECG/EKG abnormalities displaying a common or similar characteristic to an ECG/EKG strip being analyzed. In an exemplary embodiment of visual cuing device 20 adapted for use on a touch screen or other user interface, a user may be able to select an initial category of atrial, junctional or ventricular ECK/EKG abnormalities. Touch screen or user interface may then display ECG/EKG abnormalities falling within the selected category, or ECG/EKG abnormalities may be arranged into further subcategories, allowing a user to enter or select additional narrowing criteria.

In still further exemplary embodiments, visual cuing device 20 adapted for display using a touch screen or user interface may further adapted to link with internal hospital networks or other systems.

What is claimed is:

1. A visual cuing machine for heart arrhythmias comprising:
   at least twelve pivotally attached visual cuing panels having a width of no less than 5.5 inches and a height of no less than one inch;
   each of said pivotally attached visual cuing panels attached by a reinforced plastic seam which alternates the direction in which each panel pivots to allow said machine to be folded and stored; and
   each of said visual cuing panels further having a front surface and a back surface, wherein at least nine of said at least twelve visual cuing panels contain at least one visually identifiable graphically displayed EKG abnormality on at least one of said front surface and said back surface.

2. The visual cuing machine of claim 1 wherein said graphically displayed EKG abnormalities are alternated with at least one visually high-contrast, alternating solid-colored text section, wherein said at least one solid-colored text section contains at least one textual indication selected from the group consisting of an EKG abnormality name, a known EKG abnormality acronym, a known EKG abnormality abbreviation, key characteristics of an EKG abnormality, suggested treatment protocols, suggested medications, legend information, instructions on how to read and interpret ECG/EKG strips, heart diagrams, exemplary ECG/EKG waves, instructions for setting up a twelve lead ECG/EKG, and combinations thereof.

3. The visual cuing machine of claim 1 wherein more than one graphically displayed EKG abnormality is displayed on a single panel.

4. The visual cuing machine of claim 1 wherein said at least one graphically displayed EKG abnormality is scaled to a time duration of at least 6 seconds.

5. The visual cuing machine of claim 1 wherein said reinforced plastic seams are comprised of at least two continuous panel portions and an aperture reinforced with at least two layers of laminate material.

6. The visual cuing machine of claim 5 wherein said aperture is die cut.

7. The visual cuing machine of claim 1 wherein said pivotally attached visual cuing panels are capable of being rapidly opened to display at least five EKG abnormalities at one time to allow for rapid visual cuing of EKG abnormalities.

8. The visual cuing machine of claim 1 wherein said at least one EKG abnormality is selected from the group consisting of normal sinus rhythm, sinus bradycardia, sinus tachycardia, sinus arrhythmia, sinus with ST depression, sinus with ST elevation, sinus rhythm with significant Q-wave, sinus with wide QRS and inverted T-wave, sinus arrest, atrial tachycardia, sinus with paroxysmal superventricular tachycardia, Wolf Parkinson White Syndrome, atrial flutters, artifact, atrial fibrillation, multi atrial tachycardia, sinus with premature atrial contractions, sinus with premature junctional contractions, junctional escape rhythm, accelerated junctional rhythm, atrial pacing, ventricular pacing, ventricular pacing with failure to capture, atrial ventricular pacing, 1st degree heart block, 2nd degree type I, 2nd degree type II, 3rd degree heart block (complete heart block), 3rd degree AV block with junctional escape pacemaker, sinus with unifocal premature ventricular contractions, sinus with multi-focal premature ventricular contractions, sinus with episodes of non-sustained ventricular tachycardia, sinus with premature ventricular contractions converting to ventricular tachycardia (R on T), sustained ventricular tachycardia, Tor sades de pointe, ventricular fibrillation, idioventricular rhythm, accelerated idioventricular rhythm, agonal rhythm (dying heart), ventricular standstill progressing to asystole, inferior wall changes, septal wall changes, anterior wall changes, lateral wall changes, anterospetal wall changes, anterolateral wall changes, anterolateral wall injury, interior wall injury, septal wall injury, anterior wall injury, lateral wall injury, anterosepetal wall injury, ST elevation in inferior/lateral wall with reciprocal changes, left bundle branch block, and right bundle branch block.

9. The visual cuing machine of claim 1 wherein said visual cuing panels are laminated with a substance capable of being disinfected.

10. The visual cuing machine of claim 1 wherein said visual cuing panels are laminated with a substance capable of being written on with a dry-erase marker.

11. The visual cuing machine of claim 1 wherein each of said panels is comprised of at least three layers, said at least three layers being a laminate layer, a paper substrate layer, and a laminate layer.

12. The visual cuing machine of claim 1 wherein said visual cuing machine further contains a securing device for securing said visual cuing machine to a crash cart, said securing device selected from the group consisting of a binder ring, pole, chain, clamp, cord, tethering device, lynch pin, adhesives, hook-and-loop fastener, and combinations thereof.

13. The visual cuing machine of claim 1 which further includes at least one ECG/EKG strip analysis tool selected from the group consisting of a time reference line, a heart rate reference line and a baseline window.

14. The visual cuing machine of claim 1 wherein said graphically displayed ECG/EKG abnormalities are scaled between 50% and 100%.

15. The visual cuing machine of claim 1 wherein said visual cuing panels are adapted to display on a touch screen.

16. A visual cuing machine for heart arrhythmias comprising:
at least twelve pivotally attached visual cuing panels having a width of no less than 5.5 inches and a height of no less than one inch;
each of said pivotally attached visual cuing panels attached by a reinforced plastic seam which alternates the direction in which each panel pivots to allow said machine to be folded and stored;
each of said visual cuing panels further having a front surface and a back surface, wherein at least nine of said at least twelve visual cuing panels contain at least one visually identifiable graphically displayed EKG abnormality on at least one of said front surface and said back surface;
wherein said graphically displayed EKG abnormalities are alternated with at least one visually high-contrast, alternating solid-colored text section;
at least one heart rate reference line; and
at least one time reference line.

17. The visual cuing machine of claim 16 wherein said at least one heart rate reference line and at least one time reference line are disposed on an edge of a panel.

18. The visual cuing machine of claim 16 wherein said reinforced plastic seam is comprised of at least two continuous panel portions and a die cut aperture, said at least two continuous panel portions and said aperture further covered with a reinforcing laminate layer.

19. The visual cuing machine of claim 16 wherein said graphically displayed ECG/EKG abnormalities are displayed using at least two colors selected from the group consisting of black, red, and white.

20. The visual cuing machine of claim 16 wherein said text sections are displayed using at least two colors selected from the group consisting of black, white and red on a yellow background.

* * * * *